United States Patent [19]
Greelis et al.

[11] Patent Number: 6,139,535
[45] Date of Patent: Oct. 31, 2000

[54] METHOD AND APPARATUS FOR PLACEMENT AND ACTIVATION OF A MEDICAL DEVICE WITHIN A BODY CAVITY

[75] Inventors: John Patrick Greelis, Carlsbad; Mikxay Sirivong, San Diego; David G. Matsuura, Escondido; W. Tate Scott; Paul F. Zupkas, both of San Diego, all of Calif.

[73] Assignee: Situs Corporation, Solana Beach, Calif.

[21] Appl. No.: 09/322,131

[22] Filed: May 27, 1999

[51] Int. Cl.$^7$ ..................................................... A61M 5/00
[52] U.S. Cl. .......................... 604/500; 604/508; 604/514; 604/158
[58] Field of Search ..................... 604/500, 506, 604/507, 508, 511, 515, 158, 164.01, 523, 517, 514

[56] References Cited

U.S. PATENT DOCUMENTS

| | | |
|---|---|---|
| 3,498,228 | 3/1970 | Blumle et al. . |
| 3,506,005 | 4/1970 | Gilio et al. . |
| 3,650,093 | 3/1972 | Rosenberg . |
| 3,845,761 | 11/1974 | Zaffaroni . |
| 3,938,515 | 2/1976 | Leeper et al. . |
| 3,948,254 | 4/1976 | Zaffaroni . |
| 3,993,069 | 11/1976 | Buckles et al. . |
| 3,993,072 | 11/1976 | Zaffaroni . |
| 3,993,073 | 11/1976 | Zaffaroni . |
| 3,995,631 | 12/1976 | Higuchi et al. . |
| 4,012,496 | 3/1977 | Schopflin et al. . |
| 4,055,178 | 10/1977 | Harrigan . |
| 4,067,332 | 1/1978 | O'Leary . |
| 4,133,315 | 1/1979 | Berman et al. . |
| 4,155,991 | 5/1979 | Schopflin et al. . |
| 4,201,207 | 5/1980 | Buckles et al. . |
| 4,265,241 | 5/1981 | Portner et al. . |
| 4,351,337 | 9/1982 | Sidman . |
| 4,402,695 | 9/1983 | Wong . |
| 4,485,805 | 12/1984 | Foster, Jr. . |
| 4,486,190 | 12/1984 | Reinicke . |
| 4,557,726 | 12/1985 | Reinicke . |
| 4,601,707 | 7/1986 | Albisser et al. . |
| 4,626,244 | 12/1986 | Reinicke . |
| 4,684,365 | 8/1987 | Reinicke . |
| 4,690,136 | 9/1987 | van Os . |
| 4,715,852 | 12/1987 | Reinicke et al. . |
| 4,734,092 | 3/1988 | Millerd . |
| 4,813,937 | 3/1989 | Vaillancourt . |
| 4,834,704 | 5/1989 | Reinicke . |
| 4,867,743 | 9/1989 | Vaillancourt . |
| 4,871,542 | 10/1989 | Vilhardt . |
| 4,878,905 | 11/1989 | Blass . |
| 4,899,747 | 2/1990 | Garren et al. . |
| 4,904,239 | 2/1990 | Winchell et al. . |
| 4,909,790 | 3/1990 | Tsujikawa et al. . |
| 4,911,717 | 3/1990 | Gaskill, III . |

(List continued on next page.)

FOREIGN PATENT DOCUMENTS

| | | |
|---|---|---|
| 0 388 234 | 3/1990 | European Pat. Off. . |
| 1 961 671 | 12/1969 | Germany . |
| 2 077 103 | 6/1981 | United Kingdom . |
| 94/18952 | 2/1994 | WIPO . |

*Primary Examiner*—John D. Yasko
*Attorney, Agent, or Firm*—Knobbe, Martens, Olson & Bear, LLP

[57] ABSTRACT

A delivery device and method for delivering a medical device, such as an infuser, into a body cavity are disclosed. The delivery device includes an ejector tube which slidably extends through a handle. The ejector tube is configured for easy insertion through the urethra into the bladder. A hollow inner tube is located within the ejector tube and includes luer fittings at its distal and proximal ends. The luer fitting at the proximal end of the inner tube is coupled to the handle. Movement of the ejector tube relative to the inner tube causes the distal luer fitting to be withdrawn within the ejector tube and can be used to force an infuser attached to the distal luer fitting from the distal luer fitting. Materials can be transported to the infuser from the proximal luer fitting through the inner tube and out through the distal luer connector.

5 Claims, 12 Drawing Sheets

U.S. PATENT DOCUMENTS

| | | |
|---|---|---|
| 4,915,693 | 4/1990 | Hessel . |
| 4,925,446 | 5/1990 | Garay et al. . |
| 4,936,832 | 6/1990 | Vaillancourt . |
| 4,961,931 | 10/1990 | Wong . |
| 4,968,301 | 11/1990 | di Palma et al. . |
| 5,011,477 | 4/1991 | Winchell et al. . |
| 5,053,031 | 10/1991 | Borsanyl . |
| 5,061,243 | 10/1991 | Winchell et al. . |
| 5,062,829 | 11/1991 | Pryor et al. . |
| 5,067,943 | 11/1991 | Burke . |
| 5,080,652 | 1/1992 | Sancoff et al. . |
| 5,088,983 | 2/1992 | Burke . |
| 5,120,315 | 6/1992 | Hessel . |
| 5,152,747 | 10/1992 | Olivier . |
| 5,167,962 | 12/1992 | Lew et al. . |
| 5,176,360 | 1/1993 | Winchell et al. . |
| 5,211,632 | 5/1993 | Tsukada . |
| 5,219,334 | 6/1993 | Tsukada . |
| 5,224,934 | 7/1993 | Payne et al. . |
| 5,263,935 | 11/1993 | Hessel . |
| 5,284,481 | 2/1994 | Soika et al. . |
| 5,301,688 | 4/1994 | Stephen et al. . |
| 5,304,123 | 4/1994 | Atala et al. . |
| 5,318,519 | 6/1994 | Wilk . |
| 5,342,348 | 8/1994 | Kaplan . |
| 5,368,863 | 11/1994 | Eckenhoff et al. . |
| 5,429,634 | 7/1995 | Narciso, Jr. . |
| 5,476,434 | 12/1995 | Kalb et al. . |
| 5,514,096 | 5/1996 | Hiejima . |
| 5,531,688 | 7/1996 | Hiejima et al. . |
| 5,630,843 | 5/1997 | Rosenberg . |
| 5,656,032 | 8/1997 | Kriesel et al. . |
| 5,676,688 | 10/1997 | Jaker et al. . |
| 5,700,244 | 12/1997 | Kriesel . |
| 5,716,343 | 2/1998 | Kriesel et al. . |
| 5,722,957 | 3/1998 | Steinbach . |
| 5,728,396 | 3/1998 | Peery et al. . |
| 5,743,879 | 4/1998 | Kriesel . |
| 5,746,717 | 5/1998 | Aigner . |
| 5,814,019 | 9/1998 | Steinbach et al. . |
| 5,836,935 | 11/1998 | Ashton et al. . |
| 5,858,017 | 1/1999 | Demopulos et al. . |
| 5,871,478 | 2/1999 | Berrigan . |
| 5,876,377 | 3/1999 | Kriesel . |

METHOD AND APPARATUS FOR PLACEMENT AND ACTIVATION OF A MEDICAL DEVICE WITHIN A BODY CAVITY

BACKGROUND OF THE INVENTION

1. Field of the Invention

The present invention relates to a method and apparatus for delivering a medical device into a body cavity.

2. Description of the Related Art

Delivery of drugs to organs such as the bladder are typically accomplished systemically. Systemic drug delivery through oral, intravenous, intramuscular or transdermal administration methods carries with it the obvious drawbacks of any systemic treatment, such as side effects. The drug may also be metabolized or altered by physiological processes and the ultimate quantity of active drug that reaches the organ may be reduced. In addition, because many drugs are not well tolerated systemically, the dosage must be limited, thereby reducing the total effective dose that reaches the organ.

Delivery of drugs to organs such as the bladder can also be accomplished by retrograde injection of the drug into the bladder, by a catheter. Retrograde introduction of a drug by a urethral catheter, however, is suitable only for limited situations and has inherent drawbacks.

See for example, Bladder Tissue Pharmacokinetics of Intravesical Taxol, Song, D, Wientjes, M G, Au, J L, Cancer Chemotherapy and Pharmacology, 1997, 40(4): 285–92; The Pharmacokinetics of Intravesical and Oral Oxybutynin Chloride, Massad, C A, Kogan, B A, Trigo-Rocha, F E, Journal of Urology, 1992, August, 148(2 Pt 2): 595–7; Advances in Drug Delivery and Targeting, Goldstein, D, Lewis, C, Current Opinion in Oncology, 1991 Dececember 3(6): 1096–104; and Intravesical Hyaluronic Acid in the Treatment of Refractory Interstitial Cystitis, Morales, A, Emerson, L, Nickel, J C, Urology 49 (Suppl 5A): 111–113, 1997. Retrograde introduction of drug via urethral catheter is primarily used only in a hospital or managed care situation. It is not suitable for treatment of chronic urinary-tract conditions.

Stephen et al., U.S. Pat. No. 5,301,688, discloses a method for treating bladder cancers through electromotive administration of drugs into the bladder via a catheter. This type of treatment is suitable primarily for care administered on an in-patient or out-patient basis, not for chronic treatment.

Tsukada, U.S. Pat. No. 5,219,334 discloses an infuser for connection to a catheter that is suitable for long-term delivery of drug into a patient through the catheter. This device requires continuous catheterization in order to function adequately.

Pryor et al., U.S. Pat. No. 5,062,829, discloses a helical device for insertion into a body cavity, e.g., the rumen of a bovine. The helical device includes a drug that can be released over time and further includes a biodegradable portion so that, upon exhaustion of the drug, the device can break up and be naturally eliminated.

Garay et al., U.S. Pat. No. 4,925,446, discloses an infusion device having an annular shape that is suitable for delivering materials into the stomach over a prolonged period of time.

None of these prior art devices address the problem of intravesical drug delivery where drug delivery is intended to continue over a prolonged period of time while the patient maintains an active lifestyle.

Two of the major causes of urge incontinence are detrusor instability and hyperreflexia. Oxybutynin is a pharmacological agent that has been used to treat urge incontinence with some success. This drug is an anticholinergic agent that blocks contraction to the bladder and has direct smooth muscle relaxant properties. Unfortunately, this drug is associated with significant side effects upon oral administration, including dry skin, dry mouth, blurred vision, constipation, and urinary retention. In patients with cardiovascular disease, oxybutynin may lead to tachycardia. Because of the side effects, the accepted oral dose of oxybutynin is limited to 10–15 mg per day.

Interstitial cystitis is a debilitating condition in which the lining of the bladder is irritated, creating a sense of urgency and pain. The condition results in extreme frequency of urination, sometimes as many as 40, 50, or more times per day and can lead to cystectomy. Sufferers of interstitial cystitis can be treated by administration of certain drugs, including pentosanpolysulfate, manufactured by Bene of Munich, Germany and distributed by ALZA Corporation of Palo Alto, Calif. under the trademark ELMIRON. However, there is currently no satisfactory method for delivery of pentosanpolysulfate to a patient over a prolonged period of time while permitting the patient to enjoy a relatively normal lifestyle.

SUMMARY OF THE INVENTION

In one aspect of the invention, there is provides a delivery device suitable for delivering an infuser into a body cavity. The delivery device has a handle. An ejector tube extends through the handle. A hollow inner tube is disposed within the ejector tube in a sliding relationship therewith. The hollow inner tube is adapted to provide a passageway for a substance from the handle to a distal end of the hollow inner tube. The distal end of the hollow inner tube is adapted to couple to an infuser device. The ejector tube is configured to slide distally relative to the inner tube and press against the infuser device causing ejection of the infuser device from the distal end of the hollow inner tube. In one embodiment, the device has a locking mechanism configured to prevent the ejector tube from sliding with respect to the inner tube. In another embodiment, the ejector tube is configured to be passed through the urethra of a mammalian.

In another aspect of the invention, a device, such as an infuser is deliver into the organ of a patient, such as a bladder. An introducer and obturator are inserted through the urethra of the patient. The obturator is withdrawn. A delivery device is inserted through the introducer. The delivery device has a handle, an ejector tube and a hollow inner tube slidably disposed within the ejector tube. The distal end of the inner tube is coupled to the infuser. A substance is passed through the hollow inner tube from the handle to a distal end of the hollow inner tube and into the infuser device. The ejector tube slides with respect to the inner tube causing the distal end of the ejector tube to press against the infuser device, thereby ejecting the infuser device into the bladder. In one embodiment, a locking mechanism is deactivated before the step of sliding.

DETAILED DESCRIPTION OF THE INVENTION

The present invention includes a unique delivery device and method suitable for delivering an infuser device into a body cavity such as the bladder. The invention can be used to introduce an infuser such as described in co-pending U.S. patent application Ser. No. 09/041,475, filed Mar. 11, 1998, titled "Intravesical Infuser", and also described in co-pending U.S. Provisional application Ser. No. 60/130,750, filed Apr. 23, 1999, titled "Pressure Responsive Valve For Use With An Intravesical Infuser", each of which is assigned to the assignee of the present invention and incorporated in its entirety herein. The delivery device can also be utilized to deliver an infuser into a body cavity and then fill the infuser with a substance such as a drug. The delivery device can then be removed leaving the infuser in place in the body cavity.

Figure 1:
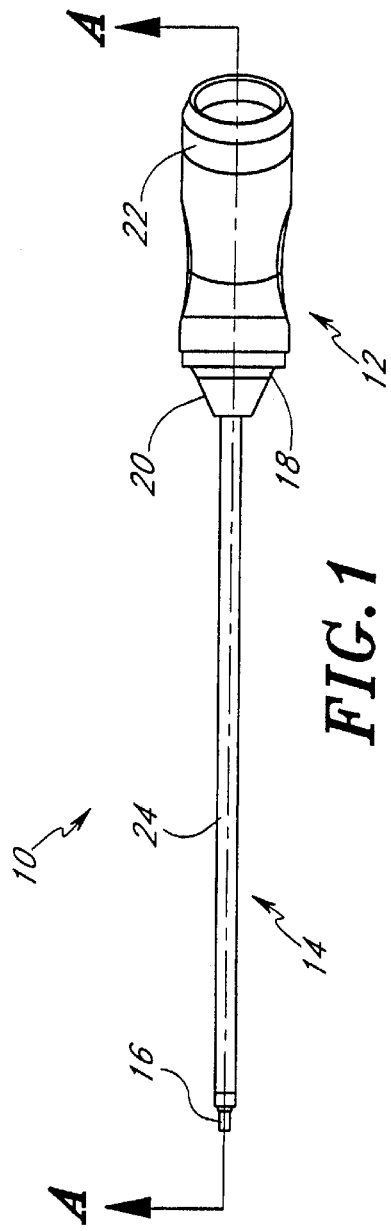
FIG. 1 is a perspective view of a delivery device.

With reference to FIG. 1, the delivery device 10 has a handle portion 12 and tube portion 14. The outer layer of the tube portion 14 visible in FIG. 1 is the ejector tube 24. A connector in the form of a distal luer fitting 16 is located at the distal end of the tube portion 14. An O-ring 18 is located at the beginning of a tapered portion 20 of the handle 12. A hollow generally cylindrical guide 22 for receiving a syringe barrel therein is located at the end of the handle 12 opposite the tube portion 14.

Figure 2:
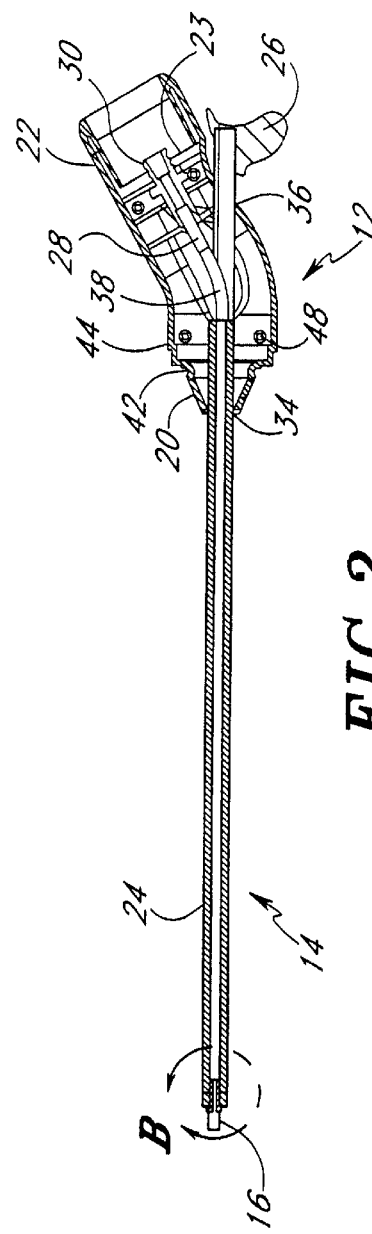
FIG. 2 is a cross-section of the delivery device of FIG. 1 taken along line A—A.
Figure 2A:
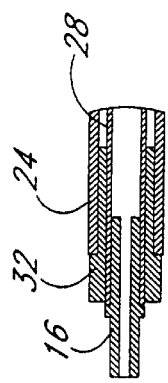
FIG. 2A is an expanded view of the distal end of the tube portion.

FIG. 2 is a cross-section of the delivery device of FIG. 1 taken along line A—A. FIG. 2A is an expanded view of the distal portion B of the tube portion 14. The tube portion 14 includes an outer layer in the form of an ejector tube 24 which extends through the handle portion 12. The ejector tube passes through a front opening 34 in the handle 12 and extends through the handle 12, exiting through a rear opening 36 adjacent to the cylindrical guide 22. A trigger 26 is attached to the end of the ejector tube 24.

A hollow, inner tube 28 is located within the ejector tube 24. The inner tube 28 and the ejector tube 24 are moveable with respect to each other. The distal end of the inner tube 28 is coupled to and in fluid communication with the distal luer fitting 16. At the proximal end, the inner tube 28 extends through an opening 38 in the wall of the ejector tube 24 within the handle 12. The proximal end of the inner tube 28 is coupled to and in fluid communication with a connector in the form of a second luer fitting 30.

The second luer fitting 30 extends from the base 23 of the cylindrical guide 22 away from the inner tube 28. The second luer fitting 30 provides a connection for a device such as a syringe. The second luer fitting 30 can be formed as an integral part of the handle 12 or it can be formed as a separate part and attached to the handle 12 with an appropriate fastening mechanism such as epoxy or a mechanical fastener. The luer fitting 30 forms an attachment point for the proximal end of the inner tube 28 and maintains the inner tube 28 in a fixed position with respect to the handle 12. The second luer fitting 30, inner tube 28 and distal luer fitting 16 form a delivery conduit. Fluid which is introduced through the luer fitting 30 can travel through inner tube 28 and exit through distal luer fitting 16.

An adapter sleeve 32 is located in the distal end of the ejector tube 24. The adapter sleeve is fixed, such as with epoxy, to the ejector tube 24 and encircles the distal portion of the inner tube 28. The adapter sleeve 32 forms the distal end of the ejector tube 24.

The ejector tube 24 is slidably retained within the front opening 34 and rear opening 36 of the handle 12. The ejector tube 24 can move slidably within those openings. The distance which the ejector tube 24 can slide is limited by the length of the opening 38 through which inner tube 28 passes. The edge of opening 38 coming into contact with inner tube 28 limits the travel of ejector tube 24.

The handle 12 includes the tapered portion 20 which extends from front opening 34 to a groove 42 which receives the O-ring 18 (not shown in FIG. 2). An outer wall 44 of the handle 12 extends from the groove 42 to the end of the cylindrical guide 22. In one embodiment the handle 12 is formed in sections which are coupled together using male and female fittings 48 and an adhesive.

Figure 3:
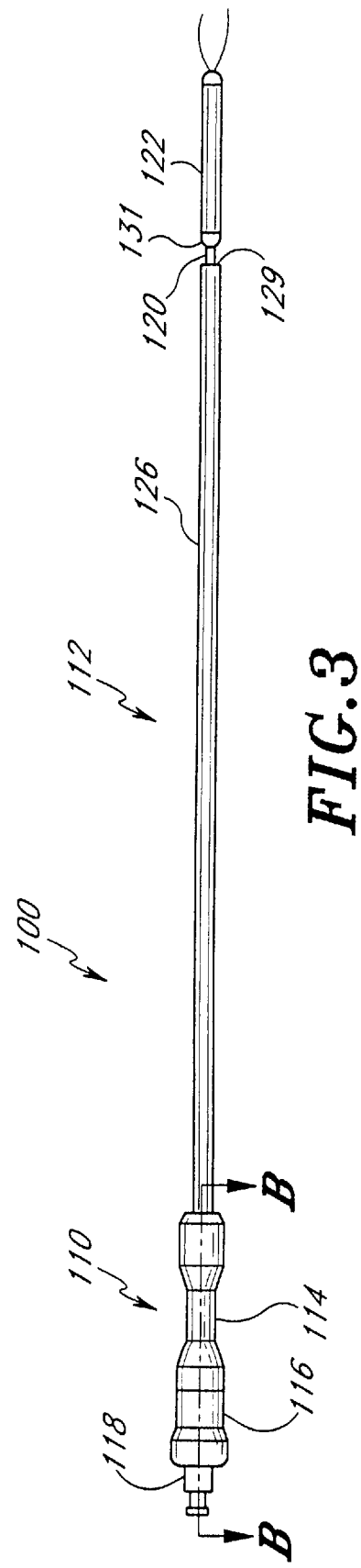
FIG. 3 is a perspective view of an alternate embodiment of a delivery device with an infuser attached.
Figure 4:
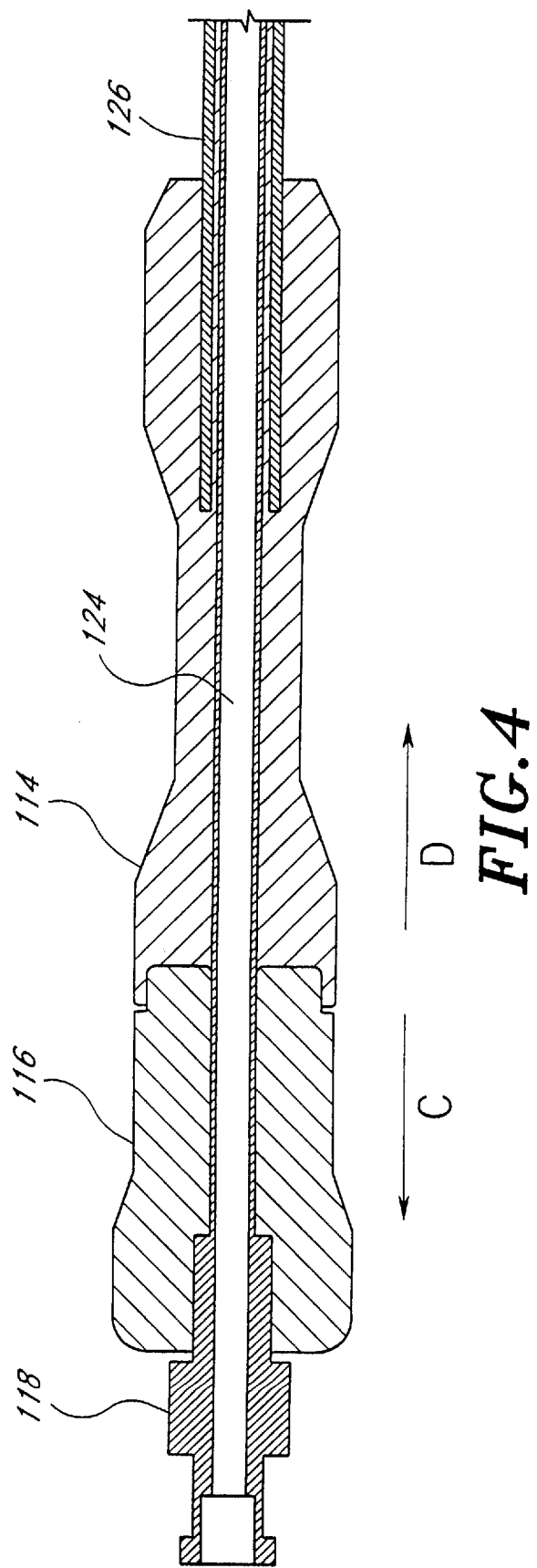
FIG. 4 is a cross-section of a portion of the delivery device of FIG. 3 taken along line B—B.

An alternative embodiment of a delivery device is depicted in FIG. 3 and FIG. 4. Referring to FIG. 3, the delivery device 100 includes a handle portion 110 and a tube portion 112. The handle portion 110 includes a front handle 114 and a rear handle 116. A proximal luer connector 118 extends from the rear of the rear handle 116. A distal luer fitting 120 is located at the distal end of the tube portion 112. An infuser device 122 is shown coupled to the distal luer fitting 120.

Referring now to FIG. 4, a hollow inner tube 124 extends through a central, tubular passageway in the front handle 114. The inner tube 124 also extends through rear handle 116 and terminates at the luer connector 118. The inner tube 124 is fastened to the rear handle 116. The fastening can be accomplished through a friction fit or through the use of a fastener such as epoxy. The inner tube 124 can slide freely within the passageway in the front handle 114 through which it passes. The inner tube 124 also extends within the length of the ejector tube 126. The distal end of the inner tube 124 is connected to and in fluid communication with the distal luer fitting 120 (see FIG. 3). The inner tube 124 also slides freely within the ejector tube 126. The luer connector 118, inner tube 124 and distal luer fitting 120 form a delivery conduit.

The ejector tube 126 extends partway into the front handle 114 and is firmly coupled to the front handle 114. The distal end of the ejector tube 126 may also include an adapter sleeve in the same manner as was described with respect to the delivery device shown in FIG. 2.

Movement of the rear handle 116 in the direction of arrow C and the front handle 114 in the direction of arrow D causes the inner tube to move in a direction opposite the movement of the ejector tube. This movement causes the distal luer fitting 120 to be withdrawn into the ejector tube. The withdrawal of the inner tube into the ejector tube causes the distal end of the ejector tube 129 (see FIG. 3) to come into contact with an end surface 131 of the infuser 122 thereby separating the infuser 122 from the distal luer fitting 120. In addition, prior to separation of the infuser 122 from the luer fitting 120, a liquid or semi-liquid can be introduced into the proximal luer connector 118, travel through the inner tube 124 and enter the infuser 122 through the distal lower fitting 120.

Figure 5:
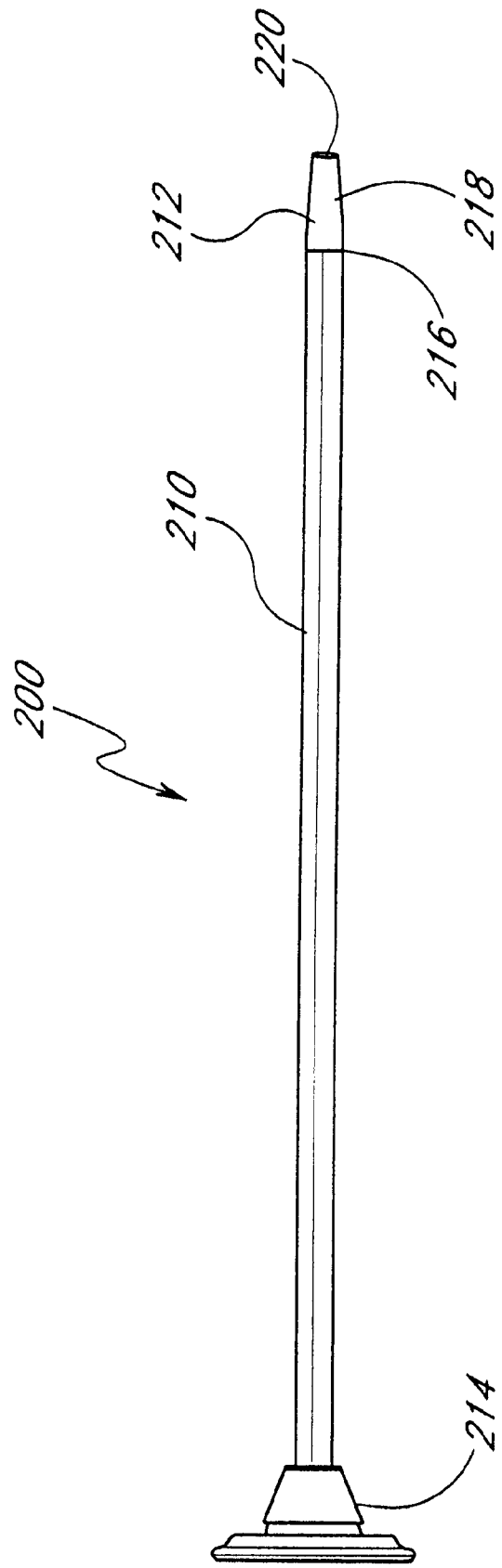
FIG. 5 is a perspective view of an obdurator.

Referring to FIG. 5, an obdurator 200 is shown. The obdurator 200 includes a rigid cylindrical shaft 210 having a dilator 212 at its distal end. The dilator 212 includes a cylindrical, tapered shaft 218 which extends distally from an opening 216 in the shaft 210 and terminates at a hemispherical tip 220. A base 214 is located at the proximal end of the obdurator 200, opposite to the dilator 212.

Figure 5A:
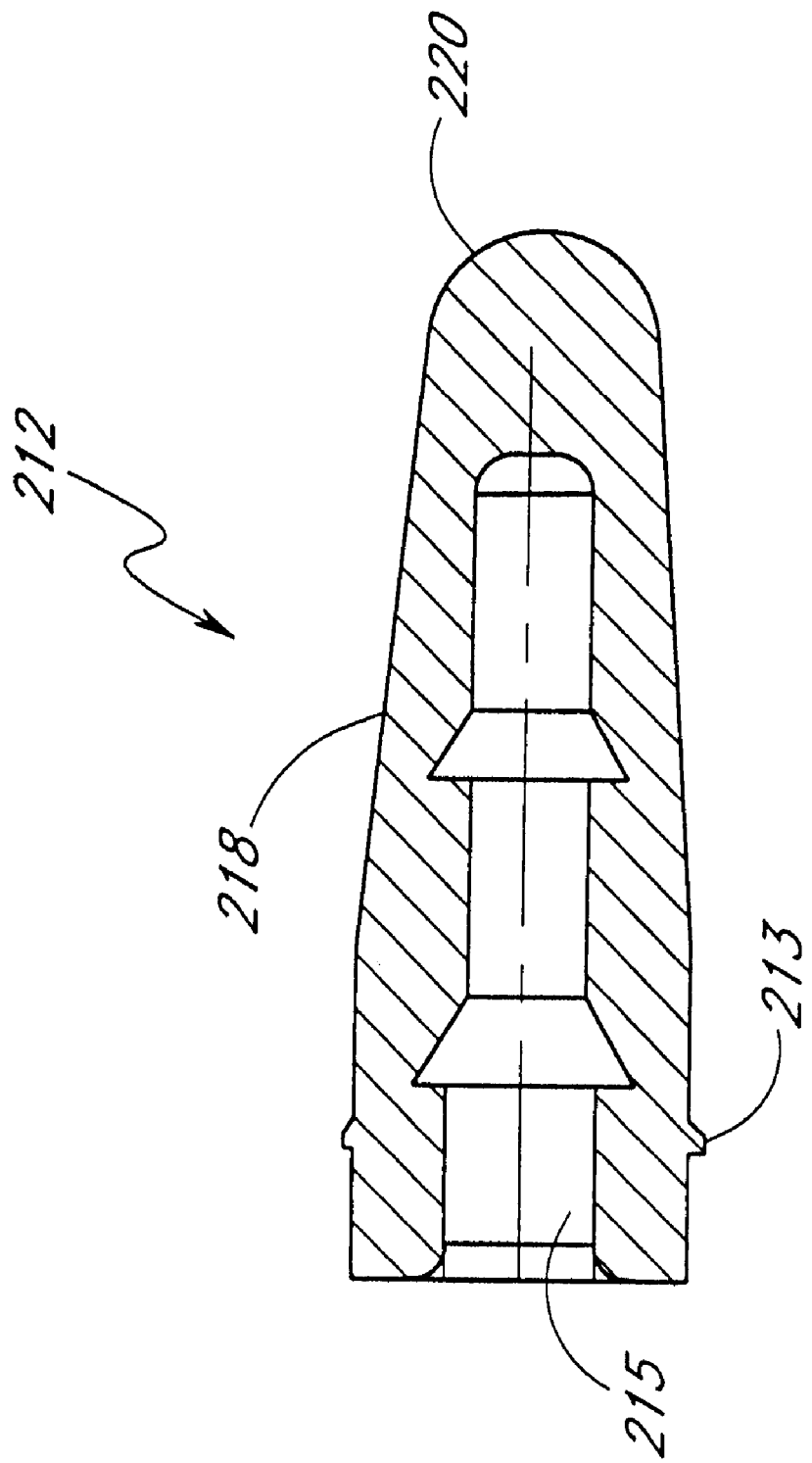

FIG. 5A is a cross-sectional view of the dilator 212. Referring to FIG. 5A, in one embodiment, the tapered shaft 218 is formed from soft, 20–50 shore A silicone and has a protrusion 213 which is configured to extend over the opening 216. A rigid portion 215 provide sufficient rigidity to the dilator 212 in order to be effective.

Figure 6:
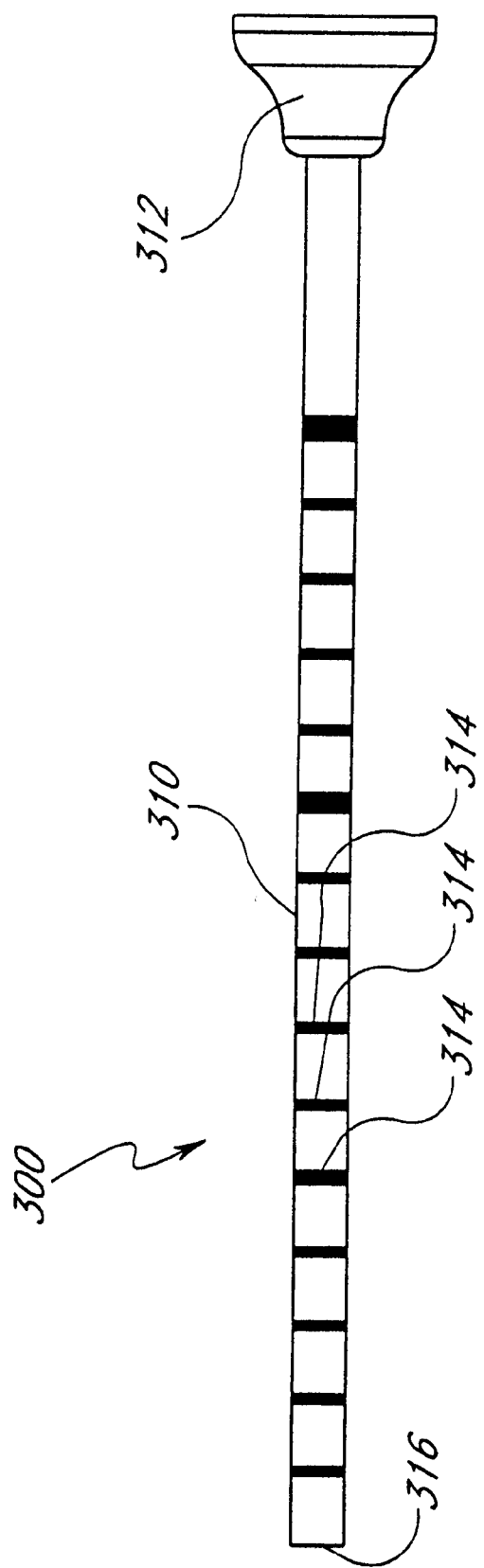
FIG. 6 is a perspective view of an introducer.

Referring to FIG. 6, an introducer 300 is depicted. The introducer 300 includes a hollow cylindrical tube 310 which extends from a hollow base 312. The hollow base 312 is configured to receive the base 214 of the obdurator 200 of FIG. 5 and the hollow tube 310 is configured to receive the shaft 210 of the obdurator. The markings 314 are placed at regular intervals along the exterior of the tube 310. The markings can be placed at intervals such as every 1 centimeter. The length of the tube 310 is such that when the obdurator 200 is fully inserted into the introducer 300, the dilator 212 of the obdurator 200 extends beyond the distal opening 316 of the introducer.

Figure 6A:
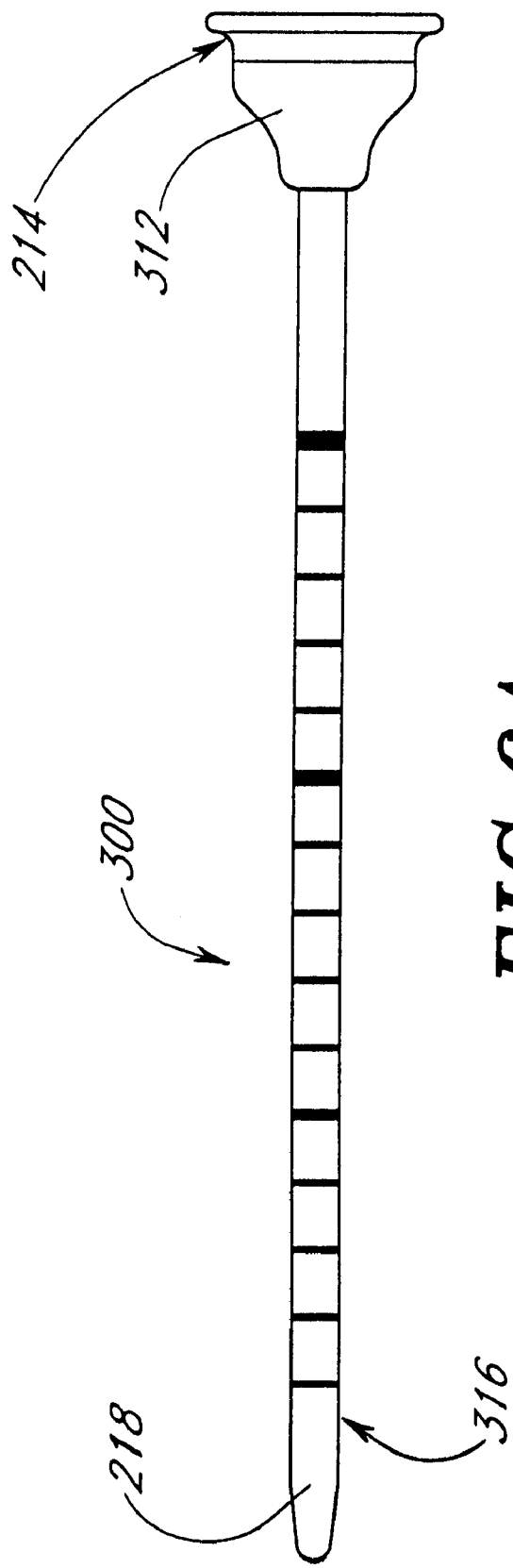
FIG. 6A is a perspective view of the obdurator installed within the introducer.

Referring to FIG. 6A, the obdurator 200 is shown as installed within the introducer 300. In one embodiment, the tapered shaft 218 is large enough to extend over the opening 316 to provide a smooth transition for the comfort of the patient, and is pliable enough to compress and be retracted through the introducer 300.

Referring now to FIGS. 7A–F, a method for delivering a device such as an infuser into a body cavity utilizing the delivery device, obdurator and introducer will be described.

Figure 7A:
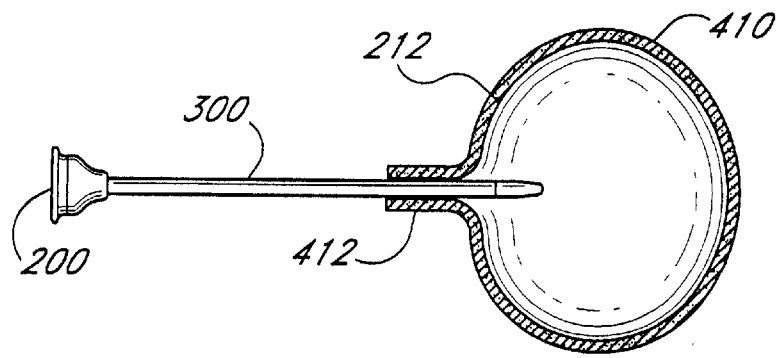
FIGS. 7A–7F represent steps in utilizing the introducer and delivery device to place an infuser into a bladder.
Figure 7B:
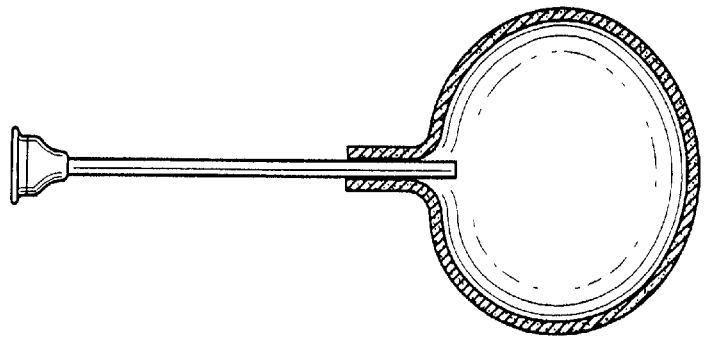

Referring to FIG. 7A, the introducer 300 is shown with the obdurator 200 fully inserted into the introducer 200 such that the dilator 212 of the obdurator extends beyond the distal end 316 of the introducer. With the obdurator fully inserted into the introducer, that combination is then inserted along the urethra 412 and into the bladder 410 of a patient. The dilator 212 is preferably formed of a material and in a shape that minimizes possible trauma to the urethra as the dilator is moved along the urethra to the bladder (see FIG. 5A). The markings 314 (see FIG. 6) on the introducer can be used to assist in determining when the distal end 316 of the introducer has entered the bladder. After the dilator and the distal end 316 of the introducer have entered the bladder 410, the obdurator is removed from the introducer leaving the introducer in place as depicted in FIG. 7B.

After the obdurator 200 has been withdrawn from the introducer 300 and the introducer remains in place, the introducer provides a pathway through the urethra 412 into the bladder 410.

Figure 7C:
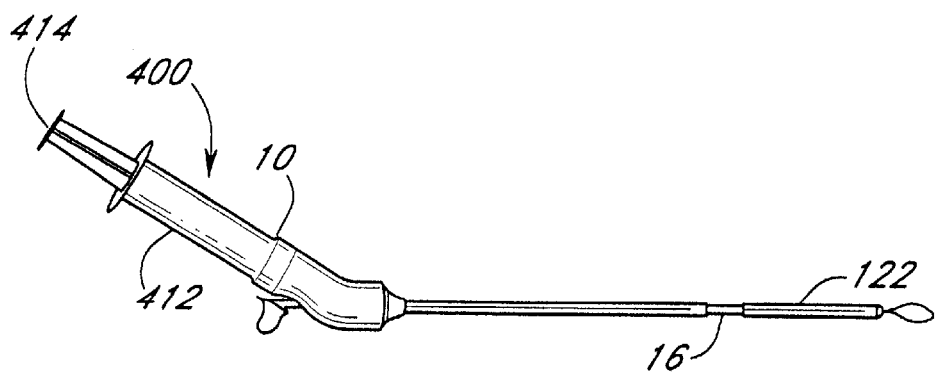

Referring to FIG. 7C, the delivery device 10 is shown having an infuser 122 coupled to the distal luer fitting 16. The barrel 412 of a syringe 400 is shown inserted into the cylindrical guide 22. A luer connector (not shown) at the end of the barrel 412 of the syringe 400 opposite to the plunger 414 has been connected to the second luer fitting 30 located within the cylindrical guide 22. Depressing the plunger 414 will cause fluid within the syringe barrel 412 to flow into the second luer fitting 30 through the inner tube 28 and out through the distal luer fitting 16 and into the infuser 122. However, prior to transferring the liquid within the syringe into the infuser, the infuser must be inserted into the bladder of the patient.

Figure 7D:
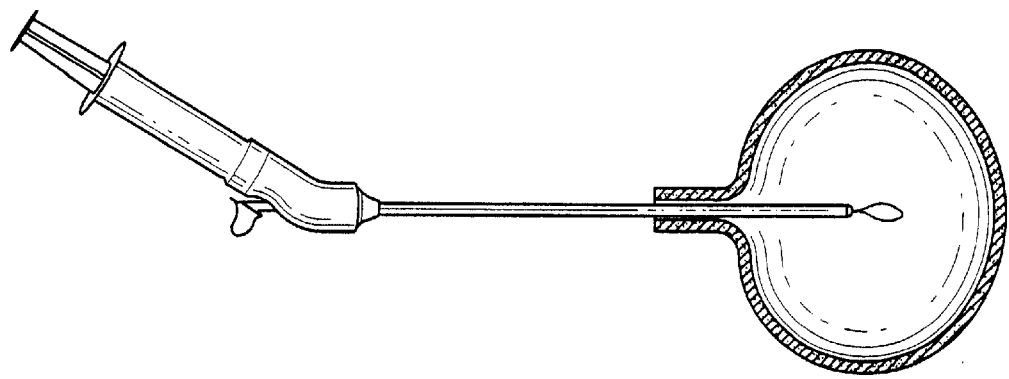

Referring to FIG. 7D, the tube portion 14 of the delivery device 10 is shown fully inserted into the introducer 300. The end of the distal luer connector reaches approximately the distal end of the introducer when the tube portion of the delivery device is fully inserted into the introducer. The infuser extends approximately completely beyond the distal end of the introducer within the bladder. Both the tube portion 14 and the infuser 122 have diameters such that they fit easily within and easily slide through tube 310. The tapered portion 20 of the delivery device 10 also fits within the hollow base 312 of the introducer when the delivery device is fully inserted into the introducer.

Figure 7E:
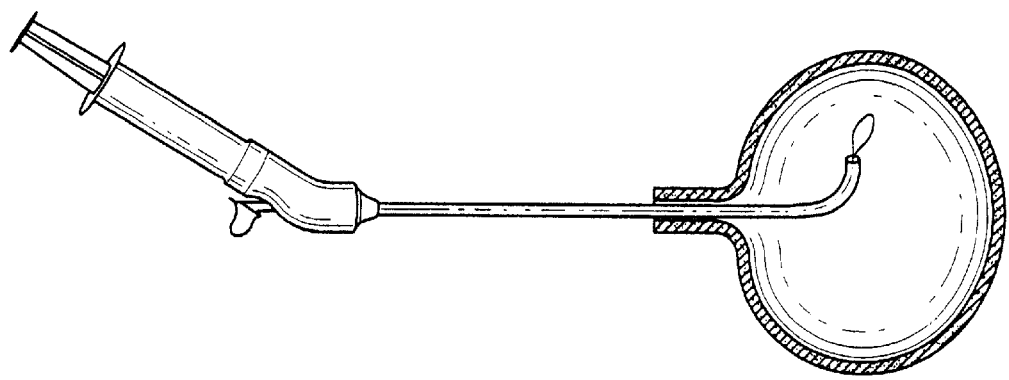

Referring to FIG. 7E, after the delivery device has been fully inserted into the introducer, the plunger 414 of the syringe is depressed, forcing the fluid contained within the syringe through the delivery device and into the infuser 122.

Figure 7F:
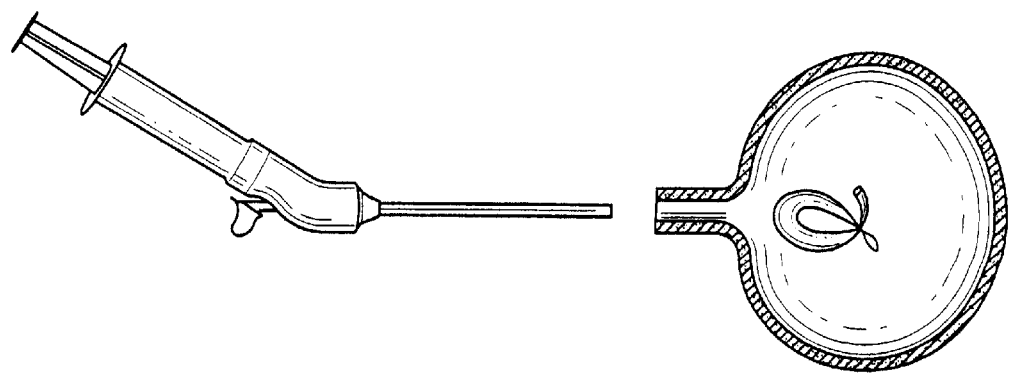

After a predetermined amount of the fluid within the syringe 400 has been transferred into the infuser 122, the trigger 26 is moved forward (towards the infuser) which causes the distal end 37 of the ejector tube 24 to come into contact with the infuser 122 and force or eject the infuser from the distal luer fitting 120. The trigger 26 is pushed forward a distance sufficient to cause the distal end of the ejector tube to travel to approximately the end of the distal luer fitting 120. Referring to FIG. 7F, the infuser is then disconnected from the delivery device and is free floating within the bladder. The delivery device and the introducer are then withdrawn through the urethra.

Figure 8A:
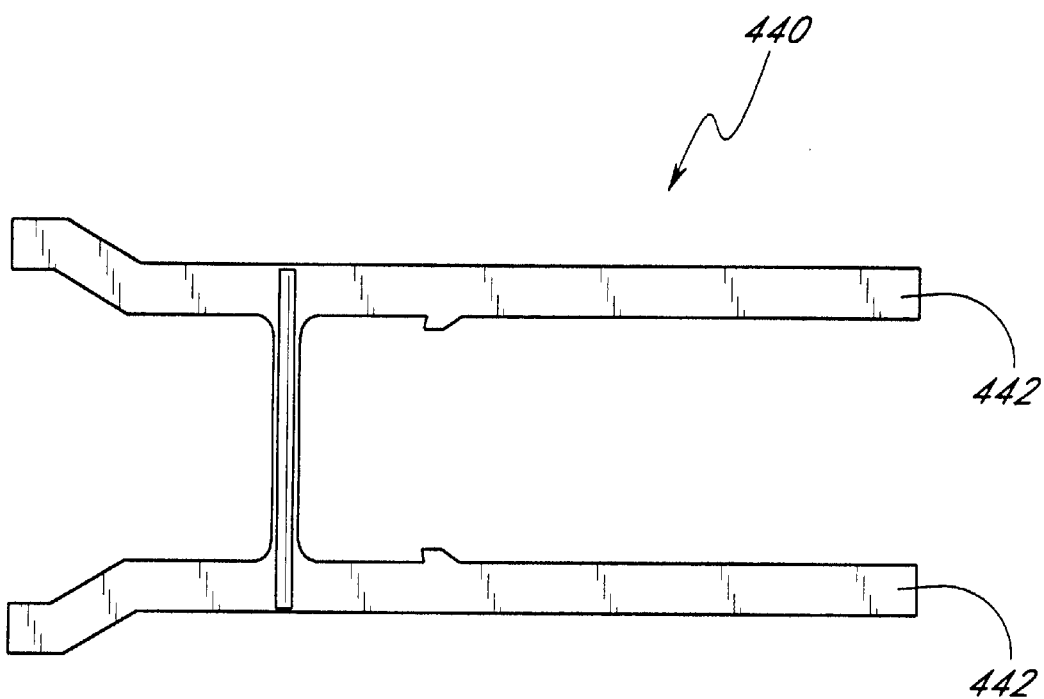
FIGS. 8A–8C are front and perspective views of a locking mechanism.
Figure 8B:
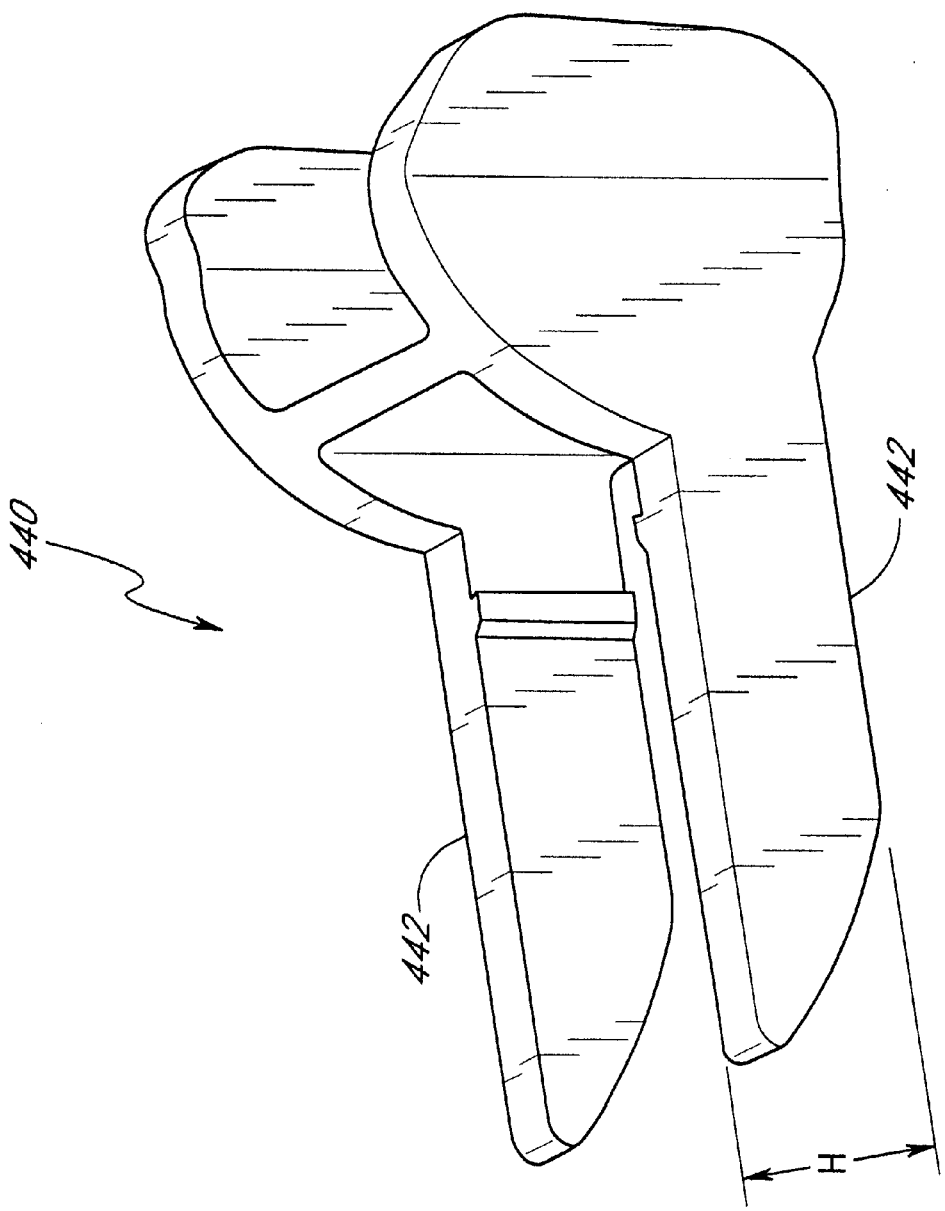
Figure 8C:
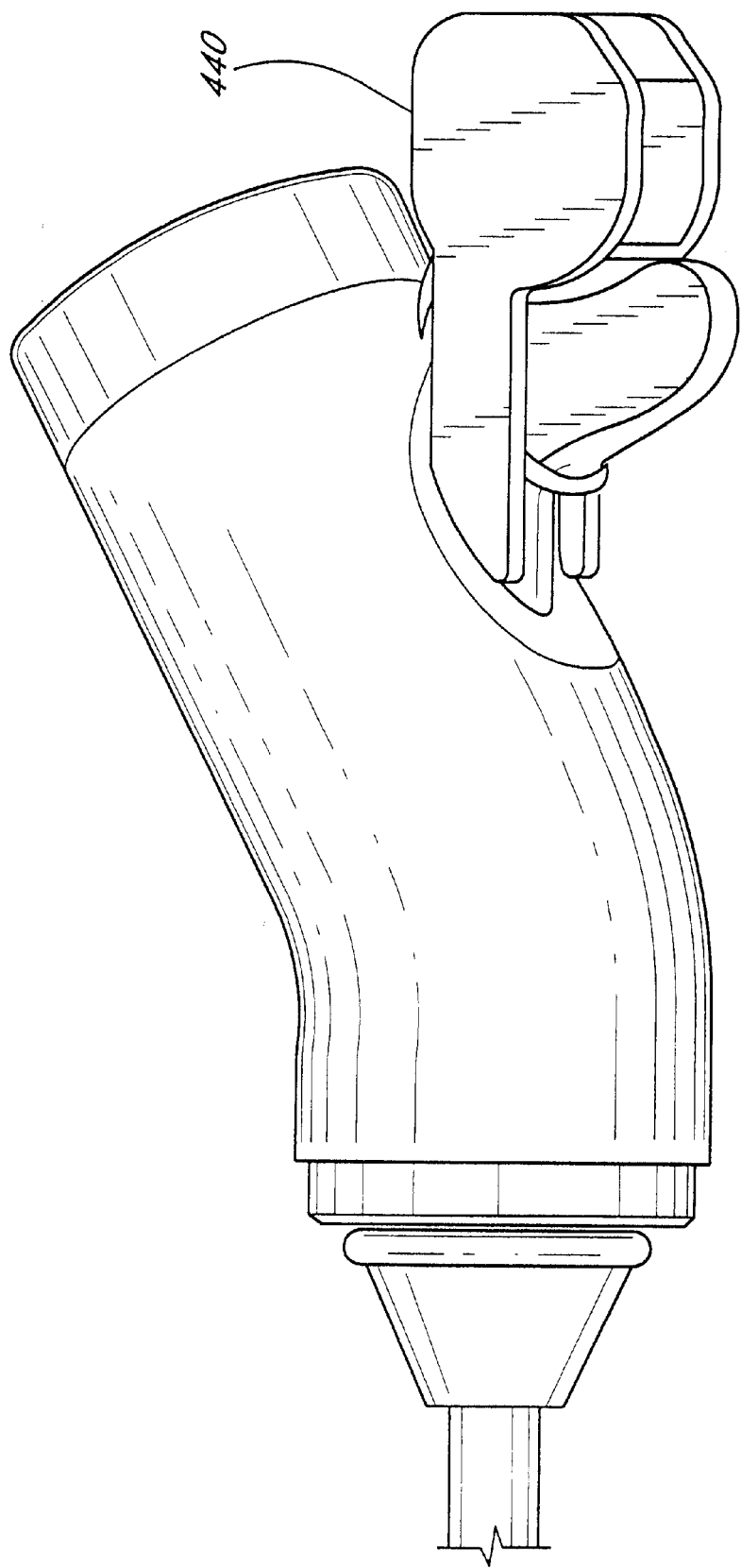

In one embodiment, a lock mechanism is used to prevent the unintentional ejection of the infuser from the distal end of the luer fitting 120. Referring to FIGS. 8A, 8B and 8C, one such locking mechanism 440 is shown in front view, in perspective view and installed on a delivery device, respectively. The locking mechanism 440 can be placed within the gap between the trigger 26 and the guide 22 such that the proximal end of the ejector tube 24 is between the extending members 442 as shown in FIG. 8C. The height, h, of the locking mechanism 440 prevents the movement of the ejector tube 24 toward the guide 22 and, thus, prevents the ejection of the infuser. The locking mechanism 440 can be in place until the infuser has been filled with drug. It can then be removed to allow the ejection of the infuser.

As was noted previously, an infuser with which the present invention finds particular usefulness is described in co-pending U.S. patent application Ser. No. 09/041,475, filed Mar. 11, 1998, titled Intravesical Infuser, and assigned to the assignee of the present invention. However, as will be appreciated by those of skill in the art, the delivery device can also be utilized to deliver other suitable objects into body cavities and to introduce liquid or semi-liquid materials into body cavities.

Although the invention has been described in terms of certain embodiments, other embodiments which will be apparent to those already skilled in the art, in view of the disclosure herein are also within the scope of this invention. Accordingly, the scope of the invention is intended to be defined only by reference to the appended claims.

What is claimed is:

1. A delivery device suitable for delivering an infuser into a body cavity, a delivery device comprising:

a handle;

an ejector tube which extends through the handle; and a hollow inner tube disposed within the ejector tube in a sliding relationship therewith, the hollow inner tube adapted to provide a passageway for a substance from the handle to a distal end of the hollow inner tube and wherein the distal end of the hollow inner tube is adapted to couple to an infuser device and wherein the ejector tube is configured to slide distally relative to the inner tube and press against the infuser device causing ejection of the infuser device from the distal end of the hollow inner tube.

2. The delivery device of claim 1 further comprising a locking mechanism configured to prevent the ejector tube from sliding with respect to the inner tube.

3. The delivery device of claim 1 wherein the ejector tube is configured to be passed through the urethra of a mammalian.

4. A method of drug delivery comprising the steps of:

inserting an introducer and obturator through the urethra;

withdrawing the obturator;

inserting a delivery device through the introducer, the delivery device comprising a handle, an ejector tube which extends through the handle, and a hollow inner tube disposed within the ejector tube in a sliding relationship therewith, the hollow inner tube adapted to provide a passageway for a substance from the handle to a distal end of the hollow inner tube and wherein the distal end of the hollow inner tube is coupled to an infuser device and wherein the ejector tube is configured to slide distally relative to the inner tube and press against the infuser device;

passing a substance through the hollow inner tube from the handle to a distal end of the hollow inner tube and into the infuser device; and sliding the ejector tube distally with respect to the inner tube causing the distal end of the ejector tube to press against the infuser device, thereby ejecting the infuser device into the bladder.

5. The method of claim 4 further comprising the step of deactivating a locking mechanism before the step of sliding.

* * * * *